United States Patent [19]

Warner

[11] 4,013,724
[45] Mar. 22, 1977

[54] SYNTHESIS OF A DITHIOL FROM 1-METHYL-2-(2-HYDROXYETHYLTHIO)-4-[1-METHYL-2-(2-HYDROXYETHYLTHIO)ETHYL]CYCLOHEXANE

[75] Inventor: Paul F. Warner, Phillips, Tex.

[73] Assignee: Phillips Petroleum Company, Hartlesville, Okla.

[22] Filed: July 24, 1975

[21] Appl. No.: 598,964

[52] U.S. Cl. .................. 260/609 D; 260/609 F; 260/47 EC

[51] Int. Cl.² .................................. C07C 149/26

[58] Field of Search ........ 260/609 D, 609 R, 609 F

[56] References Cited

UNITED STATES PATENTS

| 2,927,946 | 3/1960 | Petty | 260/609 R |
| 3,505,166 | 4/1970 | Jones et al. | 260/609 D |
| 3,652,680 | 3/1972 | Buckholz | 260/609 R |
| 3,729,518 | 4/1973 | Mulheim et al. | 260/609 D |
| 3,828,100 | 8/1974 | Hickner et al. | 260/609 D |
| 3,829,501 | 8/1974 | Hickner | 260/609 R |

OTHER PUBLICATIONS

Amer. Chem. Soc., vol. 68, pp. 1871, 2103–2104 (1946).

Primary Examiner—Lewis Gotts
Assistant Examiner—D. R. Phillips

[57] ABSTRACT

The synthesis of a new diol compound by the reaction of 2-mercaptoethanol and d,1-limonene to produce the diol 1-methyl-2-(2-hydroxyethylthio)-4[1-methyl-2-(2-hydroxyethylthio)ethyl]cyclohexane. The diol can be used as an intermediate in a reaction with a thiourea for the synthesis of a new dithiol, 1-methyl-2-(2-mercaptoethylthio)-4-[1-methyl-2-(2-mercaptoethylthio)-ethyl]cyclohexane.

3 Claims, No Drawings

SYNTHESIS OF A DITHIOL FROM 1-METHYL-2-(2-HYDROXYETHYLTHIO)-4-[1-METHYL-2-(2-HYDROXYETHYLTHIO)ETHYL]-CYCLOHEXANE

The present invention relates to a group of compounds having a structural formula of

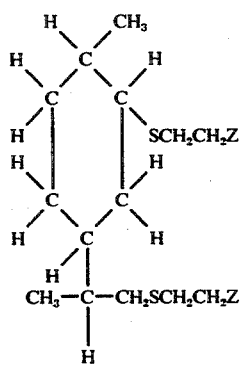

wherein the Z groups are one of OH and SH. These compounds are useful as curing agents and plasticizers with an advantage over compounds useful for the same purposes by having less objectionable odor.

It is therefore the principal object of the present invention to provide new compounds useful as curing agents which have less objectionable odor; to provide such a group of compounds wherein one of the compounds is useful as an intermediate in producing another compound.

Other objects and advantages of the present invention will become apparent from the following detailed description of the compounds and the method of making same.

Two new compounds are disclosed herein, one being a diol and the other being a dithiol wherein the diol is useful as an intermediate in producing the dithiol. The two new compounds are illustrated by the structural formulas below:

Diol        Dithiol

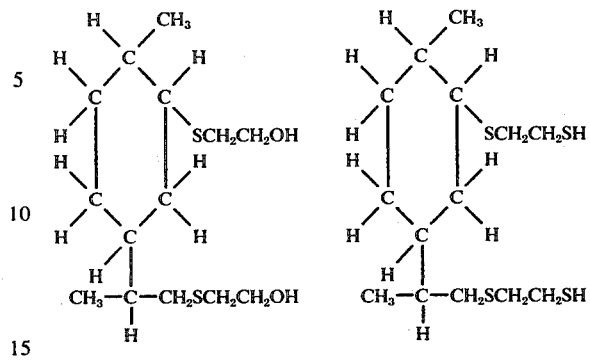

The new diol is 1-methyl-2-(2-hydroxyethylthio)-4-[1-methyl-2-(2-hydroxyethylthio)ethyl]cyclohexane. The new dithiol is 1-methyl-2-(2-mercaptoethylthio)-4-[1-methyl-2-(2-mercaptoethylthio)ethyl]cyclohexane.

The dithiol is useful as a curing agent (crosslinking agent) for epoxy resins and has a higher boiling point and less odor than related curing agents such as other dithiols and dipentene dithiol. It is believed that in the new dithiol both thiol groups are primary and should have nearly equal reaction rates whereas in dipentene-dithiol, one thiol group is primary and the other is secondary whereby the two thiol groups would have different reactivity. The new diol is useful as an intermediate for producing the dithiol and can also be used as a monomer in the production of certain polyesters and polythioesters.

PREPARATIVE PROCEDURE

The new diol is prepared by the reaction of d,1-limonene (dipentene) with 2-mercaptoethanol, preferably in the presence of a free radical initiator such as azobis-(isobutyronitrile) and peroxides such as hydrogen peroxide, organic peroxides and hydroperoxides such as butyl peroxide, benzoyl peroxide, cumene hydroperoxide, etc. UV light is also a useful initiator.

The reaction is carried out under reaction conditions to produce the new diol. The reaction conditions are as follows: the molar ratios of the reactants d,1-limonene and 2-mercaptoethanol can vary widely as, for example, between 0.1 to 10, and preferably between about 0.2 to 5.0; the temperature of the reaction can also vary widely as, for example, between 60° C to about 125° C but it is to be understood that temperatures outside of this range can also be used; the time of the reaction would be approximately 1 to about 50 hours or more and, preferably, between 10 to 30 hours.

The reaction also produces a mixture of isomeric monoadducts which are a part of the reaction mixture and have the structural formulas:

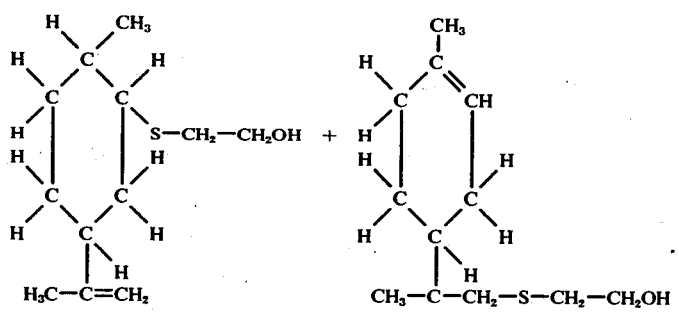

which can be recovered and recycled to the reactor for production of additional diol as detailed below. Preferably, the separation of the produced new diol is carried out by a distillation process preferably under an elevated temperature and reduced pressure. The desired product distills between approximately 180° to 188° C at approximately 3 to 10 microns of absolute pressure.

In another embodiment of the reaction to produce the new diol, the monoadducts disclosed above are formed in a first reaction using suitable reaction conditions and ratio of reactants. The monoadducts can then be reacted with additional 2-mercaptoethanol to form the desired diol.

The new diol which is produced can then be reacted with a thiourea under suitable reaction conditions to produce the new dithiol, 1-methyl-2-(2-mercaptoethylthio)-4-[1-methyl-2-(2-mercaptoethylthio)ethyl]cyclohexane. Preferably, the thiourea reaction with the new diol is carried out in an acid medium having a pH of approximately 3 or less which is used to dissolve the thiourea. Suitable acids are hydrochloric (preferred), phosphoric, sulfuric and the like in concentrations to provide the required pH and to dissolve the thiourea. Obviously, the acid employed must be one which will not degrade the reactants or products and must not interfere with the desired reaction. The diol is slowly added to the dissolved thiourea and the resulting mixture is heated to reflux temperature for a time of approximately 1 to 3 hours or more. The reaction mixture is neutralized by the addition of a base such as sodium hydroxide. The reaction conditions of the thiourea with the new diol are: the molar ratios of the thiourea and the new diol are 0.1 to 10 and, preferably, 1 to 4. The reaction is preferably carried out at the reflux temperature of the mixture. The time of the reaction may vary from about 1 to 20 and, preferably, from 2 to 10 hours.

The new dithiol is suitably separated from the reaction mixture, such as by extraction, with a suitable solvent such as toluene and purified preferably by distillation conducted at an elevated temperature and reduced pressure with the temperature being in the range of 170° to 250° C and the pressure being in the range of 1 to 10 microns Hg absolute pressure. However, it is to be completely understood that other suitable methods for purification and recovery of the new dithiol from the reaction mixture can also be employed.

Specific examples of the present invention are disclosed herein below:

EXAMPLE I

Preparation of 1-methyl-2-(2-hydroxyethylthio)-4-[1-methyl-2-(2-hydroxyethylthio)ethyl]cyclohexane:

The feedstocks used in the run were d,1-limonene (Citrus World) of 94.7 weight percent purity; 2-mercaptoethanol (BASF) of 98+ weight percent purity. Azobis(isobutyronitrile) (AIBN) from duPont was used as catalyst. A 2-liter reaction flask equipped with heating mantle, mechanical stirrer, and reflux condenser was used for the synthesis work. In making the run, 780 g (10 moles) 2-mercaptoethanol and 6 g AIBN were charged to the reactor and heated to 150° F (65.5° C). 544 g (4 moles) d,1-limonene was then added incrementally over the next hour to control the temperature. The temperature was held at 150° to 160° F (65.5°–71° C) for about 9 hours, then was raised to 180°–190° F (82.2°–87.8° C) for 23 hours to complete the reaction. After 8 hours of initial reaction time an additional 3 g AIBN was added. Samples were withdrawn at intervals and analyzed by chromatograph to follow the course of the reaction. At the end of the reaction period, the crude product was charged to a vacuum-flash unit and flashed to a final kettle temperature of 290°–300° F (143.3°–149° C) at 1.0 Hg. All of the unreacted 2-mercaptoethanol and d,1-limonene was taken overhead. The kettle product from the flash distillation was then charged to a Brush still and distilled at a pressure of 3–10 microns absolute pressure and 220°–380° F (104°–193.3° C) kettle temperature. The monadducts came over at about 335° F (168° C) and the diol product came over at 360°–380° F (182°–193° C). The distillation was continued until the kettle was essentially dry, leaving a small quantity of black tar as kettle product.

The diol product, 1-methyl-2-(2-hydroxyethylthio)-4-[1-methyl-2-(2-hydroxyethylthio)ethyl]cyclohexane, weighed 704 g (2.41 moles) and had a purity of 98.7%. The yield, based on d,1-limonene charged, was 60.1% of theoretical.

EXAMPLE II

Another run was made to prepare the diol, using the following reactants and catalyst:
- 780 g (10 moles) 2-mercaptoethanol
- 408 g (3 moles) d,1-limonene
- 6 g AIBN catalyst charged initially; 3 g additional AIBN was charged after approximately 7 hours.

The initial reaction temperature was 152° F (66.67° C) which rose slightly to 162° F (72.22° C) and then was maintained between 155°–161° F (68.33°–71.67° C) for 20 hours. The temperature was then raised to the range 180°–210° F (82.22°–98.9° C) for 3 hours.

1192 g crude product was recovered. After distillation as in Example I, 736 g of the diol was recovered. The purity of this sample by gas chromatography was 99%. The yield based on d,1-limonene was 83.3% of theoretical. This shows that higher mole ratios of 2-mercaptoethanol to d,1-limonene are desirable.

EXAMPLE III

The overhead cuts from the flash distillation of Examples I and II, containing 2-mercaptoethanol, and the overhead product from the low-pressure Brush distillation, comprising mainly the monoadducts, were combined in this run together with additional fresh feed to illustrate potential use of recycle material in a projected semi-continuous or continuous process for production of additional diol. This was a batch run. Materials used:

|  | grams |
| --- | --- |
| 2-mercaptoethanol | |
| recycle | 605 |
| fresh | 234 |
| Monoadducts (recycle) | 259 |
| Diol product[1] | 54 |
| d,l-limonene | 272 |
| AIBN | 7.0 initially+ |
| | 3.5 g after 7 hours |

[1]This amount of diol was carried over with the monoadduct during the distillation and was not separated. Composition of the fraction was determined by GLC.

All ingredients were charged simultaneously and the temperature was maintained between 145°–160° F (62.8°–71.1° C) for 20 hours. The temperature was then raised to 180°–192° F (82.2°–88.9° C) and kept in that range for 6 hours. 806 g of product diol was recovered. The run demonstrates that materials can be used which have been recovered from prior batch runs. In such processes the use of recycle material is economically important.

Table I

Properties and Compositions of Diol Product Made From 2-Mercaptoethanol and d,l-Limonene The final diol products produced in all runs, constituting the new diol 1-methyl-2-(2-hydroxyethylthio)-4-[1-methyl-2-(2-hydroxyethylthio)ethyl]-cyclohexane, with minor impurities (about 2%), were combined and the following properties determined:

| | |
| --- | --- |
| Refractive Index 20/D | 1.5416 |
| Specific Gravity 60/60 F | 1.1080 |
| Mole Weight | 306[1] |
| Total Sulfur, wt. percent | 21.6 (calc. 21.98) |
| Mercaptan Sulfur, wt. percent | 0.05 |
| Color, Gardner | 5 |
| Viscosity at 100 F, centistokes | 386.0 |
| Boiling Point | 419° F (1 mm Hg.) (215° C) |
| Composition by Chromatograph, wt. percent | |
| Lights | 0.4 |
| Monoadducts | 1.6 |
| 1-methyl-2-(2-hydroxyethylthio)-4-[1-methyl-2-(2-hydroxyethylthio)ethyl]cyclohexane | 98.0 |
| Total | 100.0 |

[1]By Osmometer, the calculated molecular weight of the diol is 292.

EXAMPLE IV

Preparation of 1-methyl-2-(2-mercaptoethylthio)-4-[1-methyl-2(2-mercaptoethylthio)ethyl]cyclohexane:

A 2-liter reaction flask equipped with thermowell, motor-driven stirrer, and reflux condenser was used. HCl, 3.4 moles (36–38% HCl) and thiourea, 258 g (3.4 moles) were charged to the reactor and heated gently until the thiourea was all in solution. The diol (combined product from all above runs), 438 g (1.5 moles), was then added incrementally over a period of 15 minutes while the temperature was being brought to 220° F (104.4° C). There was no noticeable rise in temperature. The mixture was held at reflux, 220° F, for 5¼ hours, then 3.6 moles NaOH in 432 g water was added slowly from a dropping funnel. The caustic was added over a period of about 20 minutes.

The mixture was cooled to room temperature and let stand overnight. In the morning, 200 g toluene and 41 ml HCl (½ mole) was added to bring the pH to 4–5 to aid in phase separation and to extract the dithiol product into the organic phase; the mixture was again heated to reflux, 215° F (102° C). After 15 minutes the mixture was transferred to a separatory funnel. The water phase was drawn off, and the organic phase containing the dissolved dithiol product was washed with 200 ml hot water. Phase separation was poor during the wash step but was finally accomplished by heating to boiling and addition of 70 g solid NaCl (to increase density of water phase).

The organic phase, 661 g, was charged to a 1-plate vacuum flash unit and flashed to a kettle temperature of 300° F (149° C) at 1 mm Hg. The organics recovered as kettle product, 481 g, had a mercaptan sulfur content of 18.46 wt. percent. This was charged to a Brush still and distilled at a kettle temperature of 345°–400° F (174°–204.4° C) at 3 microns Hg absolute pressure. Cut 1, 55 g, was discarded.

The yield of 99.9 purity dithiol (cut 2 Brush still) was 73.3 percent of theoretical based on diol (Product I) charged.

The 99.9 percent pure product had the following properties:

| | |
| --- | --- |
| Boiling Point (1 mm Hg.) | 432° F (222.22° C) |
| Refractive Index 20/D | 1.5722 |
| Specific Gravity 60/60° F (15.56° C) | 1.1156 |
| Total Sulfur, wt. % | 39.1(calculated 39.4) |
| Mercaptan Sulfur, wt. %[1] | 18.74 |
| | 19.74(calculated 19.7) |
| | 19.14 |
| Viscosity, centistokes at 37.78° C (100° F) | 34.7 |
| Color, Gardner | 1 |

[1]Three different analyses were made which resulted in different values all of which are reported here.

In order to illustrate the usefulness of the new dithiol as a curing agent the following example is provided:

EXAMPLE V 1-methyl-2-(2-mercaptoethylthio)-4-[1-methyl-2-(mercaptoethylthio)ethyl]cyclohexane as curing agent for epoxides:

10 g Shell Epoxy Resin Epon 828[1]

8.5 g dithiol
10 drops bis(N,N-dimethylaminomethyl)phenol[2]

(1) Reaction product of Bisphenol A and glycidyl oxide (Shell Oil Co.)
(2) DMP-30 (Rohm & Haas)

The above ingredients were mixed in a small aluminum dish and allowed to stand. The mixture set in about 20 minutes, was dry to the touch in 30 minutes and cured to a hard, brittle layer in 8 hours. No odor was noticed.

It is to be understood that while I have described certain forms of my invention, it is not to be limited to the specific disclosure herein which is merely exemplary of the invention which may be embodied in other forms. Therefore the specific disclosure herein is not to be interpreted as limiting, but merely as a basis for the claims and as a representative basis for teaching one skilled in the art to variously employ the present invention in virtually any appropriate manner.

What I claim and desire to secure by letters patent is:

1. A group of compounds having a structural formula of

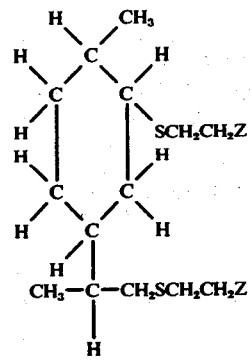

where the Z group is one of OH and SH but not both in the same compound.

2. A compound as set forth in claim 1 wherein the Z groups are OH and the compound is known as 1-methyl-2-(2-hydroxyethylthio)-4-[1-methyl-2-(2-hydroxyethylthio)ethyl]cyclohexane.

3. A compound as set forth in claim 1 wherein the Z groups are SH and the compound is known as 1-methyl-2-(2-mercaptoethylthio-4-[1-methyl-2-(2-mercaptoethylthio)ethyl]cyclohexane.

* * * * *